United States Patent [19]

Sakurada

[11] 4,346,056
[45] Aug. 24, 1982

[54] AUTOMATIC ANALYZING APPARATUS

[75] Inventor: Masahiko Sakurada, Machida, Japan

[73] Assignee: Olympus Optical Company Limited, Tokyo, Japan

[21] Appl. No.: 177,446

[22] Filed: Aug. 11, 1980

[30] Foreign Application Priority Data

Aug. 15, 1979 [JP] Japan ............................ 54/111525[U]
Aug. 17, 1979 [JP] Japan ............................ 54/112413[U]

[51] Int. Cl.³ ............................................ G01N 35/04
[52] U.S. Cl. ........................................ 422/64; 422/67
[58] Field of Search .................... 422/63, 64, 65, 67; 364/497

[56] References Cited

U.S. PATENT DOCUMENTS

| | | | |
|---|---|---|---|
| 3,770,382 | 11/1973 | Carter et al. | 422/67 X |
| 3,917,455 | 11/1975 | Bak | 422/65 X |
| 4,058,367 | 11/1977 | Gilford | 422/67 X |
| 4,234,539 | 11/1980 | Ginsberg et al. | 422/67 X |
| 4,267,149 | 5/1981 | Bruckner et al. | 422/67 X |

Primary Examiner—Ronald E. Serwin
Attorney, Agent, or Firm—Stevens, Davis, Miller & Mosher

[57] ABSTRACT

An automatic analyzing apparatus comprising a plurality of reagent vessels adapted to be inserted into a reagent vessel holder and a detector for photoelectrically discriminating the reagent vessel holder in response to an analysis item necessary for examining an organic ability and the reagent vessels corresponding to different analysis items.

9 Claims, 10 Drawing Figures

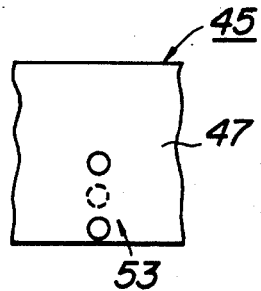
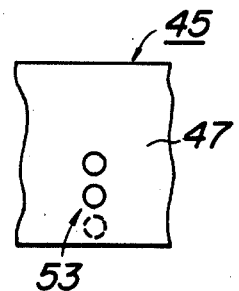
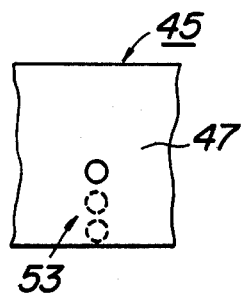
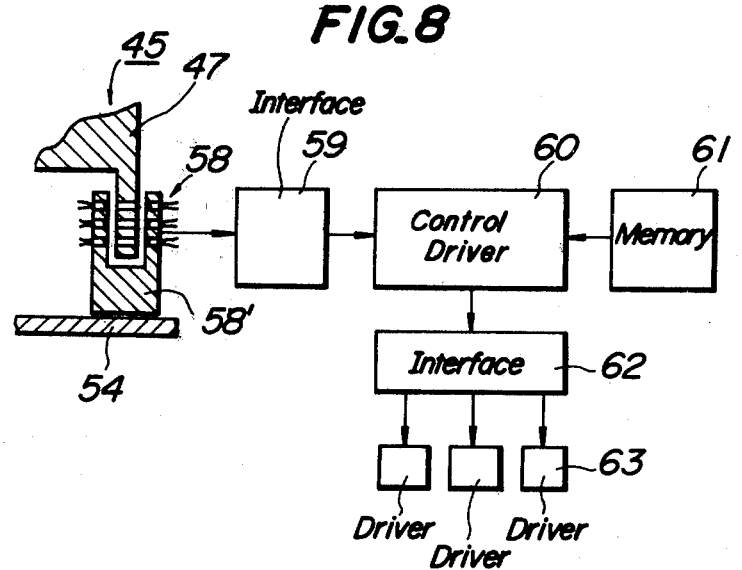

AUTOMATIC ANALYZING APPARATUS

BACKGROUND OF THE INVENTION

1. Field of the Invention

This invention relates to an automatic analyzing apparatus.

2. Description of the Prior Art

Various kinds of automatic analyzing apparatuses, in which a collected sample such as serum, urine or the like and a reagent necessary for analyzing a desired composition contained in the sample are injected into a reaction cuvette to prepare a test liquid and the test liquid is subjected to a colorimetric measurement so as to effect a quantitative analysis on the desired composition contained in the sample, have heretofore been proposed. But, in such conventional automatic analyzing apparatus, when an analysis item is set an operator is generally required not only to effect an operation of setting a reagent to be used, but also to effect an operation of setting various conditions in response to analysis items such as an amount of sample to be injected, amount of reagent to be injected, photometric wave length, or the like or effect an operation of calling out the above mentioned analysis conditions in response to the analysis items which have been supplied as inputs beforehand. As a result, the conventional automatic analyzing apparatus has the disadvantage that it is complex in operation and that there is a risk of the erroneous operation being induced.

Meanwhile, the automatic analyzing apparatus can generally analyze at least 30 items, whereas desired average number to be analyzed for one sample is on the order of 6 to 8. As a result, the conventional automatic analyzing apparatus is constructed such that it can simultaneously analyze 6 to 12 channels, that is, 6 to 12 analysis items. In such automatic analyzing apparatus, if it is desired to analyze more than 12 analysis items, initially the apparatus is set to that number of analysis items which can be analyzed at one time and the analysis is effected. Subsequently, the apparatus is set to the remaining analysis items and the analysis is effected again. As a result, the conventional apparatus has the drawback that the operations of setting the reagent and of setting the analysis condition for each analysis item become more complex and that there is a risk of erroneous operation being induced.

SUMMARY OF THE INVENTION

An object of the invention, therefore, is to provide an automatic analyzing apparatus which can reliably set the analysis items by means of a simple operation.

A feature of the invention is the provision of an automatic analyzing apparatus comprising means for discriminating kinds of reagent, a memory for storing analysis conditions for all of the analysis items such as an amount of sample to be injected, amount of reagent to be injected, photometric wave length, or the like, and a control device for controlling said means in response to the analysis condition read out from said memory.

Further objects and features of the invention will be fully understood from the following detailed description with reference to the accompanying drawings, wherein:

BRIEF DESCRIPTION OF THE DRAWINGS

FIGS. 7A, 7B and 7C are diagrammatic views illustrating three discriminative examples of the reagent vessel holder shown in FIG. 6; and FIG. 8 is a diagrammatic view showing a control circuit of an automatic analyzing apparatus shown in FIG. 4.

DETAILED DESCRIPTION OF THE PREFERRED EMBODIMENTS

Figure 1:
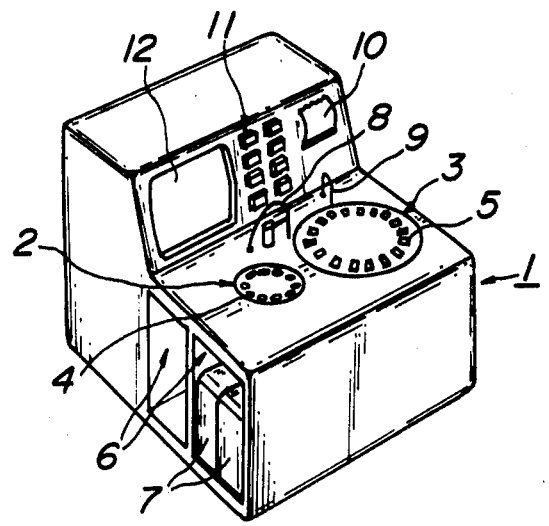
FIG. 1 is a perspective view of one embodiment of an automatic analyzing apparatus according to the invention.
Figure 2:
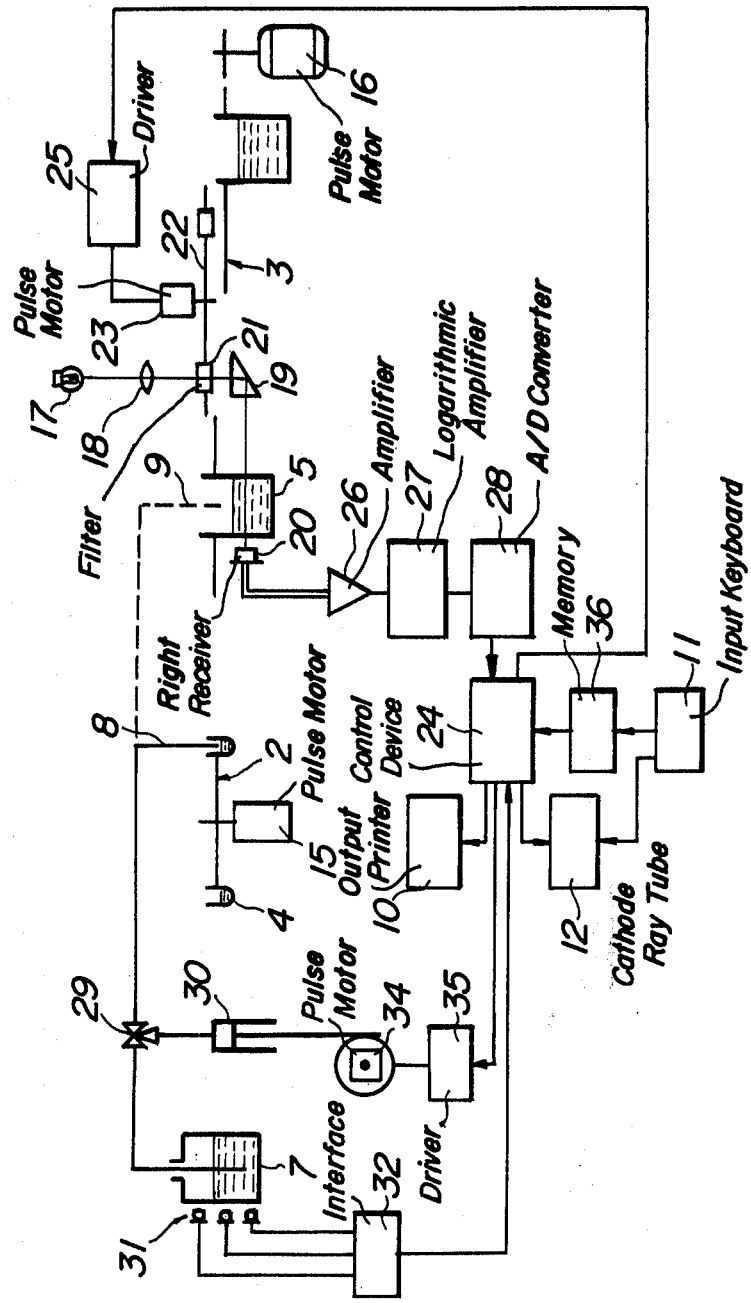
FIG. 2 is a diagrammatic view showing an arrangement of essential parts of the automatic analyzing apparatus shown in FIG. 1.

FIG. 1 shows one embodiment of an automatic analyzing apparatus according to the invention. On the apparatus main body 1 are rotatably mounted a sampler 2 and reaction disc 3, these sampler and reaction disc being intermittently rotatable with a constant period. A plurality of sample cups 4 containing collected serum, urine or the like are arranged along the same circle having a center at the rotary axis of the sampler 2 and equidistantly separated one from the other. A plurality of cuvettes 5 are held by the reaction disc 3 and arranged along the same circle having a center at the rotary axis of the reaction disc 3 and equidistantly spaced apart from each other. The apparatus main body 1 is also provided with a compartment 6 formed in the apparatus main body 1 and detachably enclosing therein a plurality of reagent vessels 7 containing given reagents necessary for desired analysis items and with a detector 31 as shown in FIG. 2 and for discriminating the reagent vessels 7 one from the other. The apparatus main body 1 is provided with a probe 8 connected to a syringe 30 as shown in FIG. 2. The probe 8 functions to suck in, at a given sucking position, the sample in each sample cup 4 held by the sampler 2 and inject a given amount of the sample thus sucked together with the reagent in the given reagent vessel 7 set in the reagent vessel mounting member 6 to each reaction cuvette 5 held by the reaction disc 3. The reaction disc 3 is provided at its periphery with a probe 9 connected to a syringe (not shown). The probe 9 functions to inject a given amount of reagent in another given reagent vessel 7 set in the compartment 6 as a second reagent to each reaction cuvette 5 located at a position which is taken by each reaction cuvette 5 after the lapse of a given time from the exhaust position of the probe 8. In this way, the sample and second reagent are injected into the reaction cuvette 5 to prepare a test liquid. Then, during a given time, the reaction cuvette 5 is transferred to a position where the test liquid is subjected to the colorimetric measurement with the aid of a filter 21 which allows to pass a light having a given wave length therethrough in response to the analysis item. The measured value and concentration conversion factor in response to the analysis item cause the desired analysis to be displayed by an output printer 10. In addition, the apparatus main body 1 is provided with an input keyboard 11 for causing a memory 36 to store beforehand analysis conditions such as an amount of sample to be injected, amount of reagent to be injectd, photometric wave length, or the like. The apparatus main body 1 is also provided with a monitor cathode ray tube 12 for displaying the input information, analysis data or the like delivered from the input keyboard 11.

As shown in FIG. 2, provision is made of a control device 24 for controlling the analysis operation in response to the analysis condition for each analysis item. The control device 24 is constructed such that it functions to read out the analysis condition for the analysis item corresponding to the reagent discriminated by the memory 36 and control the analyzing operation of the desired analysis item.

FIG. 2 shows essential parts of the automatic analyzing apparatus shown in FIG. 1. Same reference numerals designate the same parts throughout FIGS. 1 and 2. To the center shaft of the sampler 2 is secured an output shaft of a pulse motor 15. The pulse motor 15 functions to intermittently rotate the sampler 2 with a constant period. The reaction disc 3 is provided at its periphery with a gear threadedly engaged with a gear secured to an output shaft of a pulse motor 16. The reaction disc 3 is so constructed that it is rotated intermittently with a given period in synchronism with the rotation of the sampler 2.

In the present embodiment, the reaction disc 3 is provided at its center portion with an opening in which is fitted a photometric device for effecting colorimetric measurement of the test liquid prepared in the reaction cuvette 5. The photometric device is constructed such that a light ray emitted from a polychromatic light source 17 arranged on the rotational center axis of the reaction disc 3 is incident on a lens 18 to obtain a parallel light flux which is then incident through a prism 19 on the reaction cuvette 5 arranged at a given photometric position of the reaction disc 3, that the light transmitted through the reaction cuvette 5 and the test liquid contained therein is received by a light receiver 20, and that in the photometric light passage between the light source 17 and the light receiver 20 is selectively inserted a filter 21 that functions to transmit therethrough a light having a given wave length in response to the analysis item. In the present embodiment, the filter 21 functions to transmit lights used for various analysis items and having different wavelengths and is held on the same circle having a center at the center axis of a filter holding member 22. The filter holding member 22 is rotatably supported at its center axis and driven by a pulse motor 23 connected to the center axis of the filter holding member 22 and inserted into the photometric passage. The pulse motor 23 is driven through a driver 25 from the control device 24. The output from the light receiver 20 is supplied through an amplifier 24, logarithmic amplifier 27 and analog-digital converter 28 to the control device 24.

The probe 8 is connected through a change-over valve 29 to the syringe 30 and to that reagent vessel 7 which contains a reagent used as a diluent and which is set in the compartment 6. The reagent vessel 7 set in the reagent vessel mounting member 6 is discriminated by a detector 31 arranged in opposition to the reagent vessel 7. The discrimination signal delivered from the detector 31 is supplied through an interface 32 to the control device 24.

Figure 3:
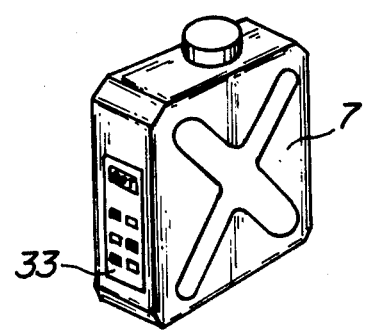
FIG. 3 is a perspective view of a reagent vessel used in the automatic analyzing apparatus shown in FIG. 1.

In the present embodiment, to each reagent vessel 7 used for various analysis items is attached a label 33 as shown in FIG. 3. The label 33 is provided thereon with code marks corresponding to the kinds of reagents contained in the reagent vessel 7 and to analysis item, for example, "GOT". The detector 31 functions to photoelectrically read out these code marks.

In FIG. 2, the syringe 30 is driven by a pulse motor 34 so as to effect its injection operation and control the amount of sample to be injected and amount of diluent to be injected in response to the analysis item. The driving control operation of the pulse motor 34 is effected through a driver 35 from the control device 24.

Similar to the probe 8, the probe 9 for injecting the second reagent to the reaction cuvette 5 is connected through the change-over valve 29 to the syringe 30 and to another given reagent vessel 7 set in the compartment 6. The amount of sample and second reagent to be injected by the syringe 30 is also controlled in response to the analysis item by means of the control device 24. Similarly, the reagent vessel 7 connected to the probe 9 is also discriminated by the detector 31 and the discrimination signal thus obtained is supplied to the control device 24.

A memory 36 functions to store the analysis items of all of the analyzable items delivered from an input keyboard 11 and supply the analysis condition of a given analysis item to the control device 24. The control device 24 functions to read out the analysis condition for the analysis items which have been stored in the memory 36 and corresponding to the reagent discriminated by the detector 31 and control the operation of the above described members such as the pulse motors 23, 34 or the like on the basis of the analysis condition and select the given concentration conversion factor so as to control the desired analysis item.

As stated hereinbefore, the present embodiment renders it possible to reliably set the desired analysis item by the simple operation of setting the reagent vessel 7 containing the given reagent necessary for the desired analysis item in the reagent vessel mounting member 6.

Figure 4:
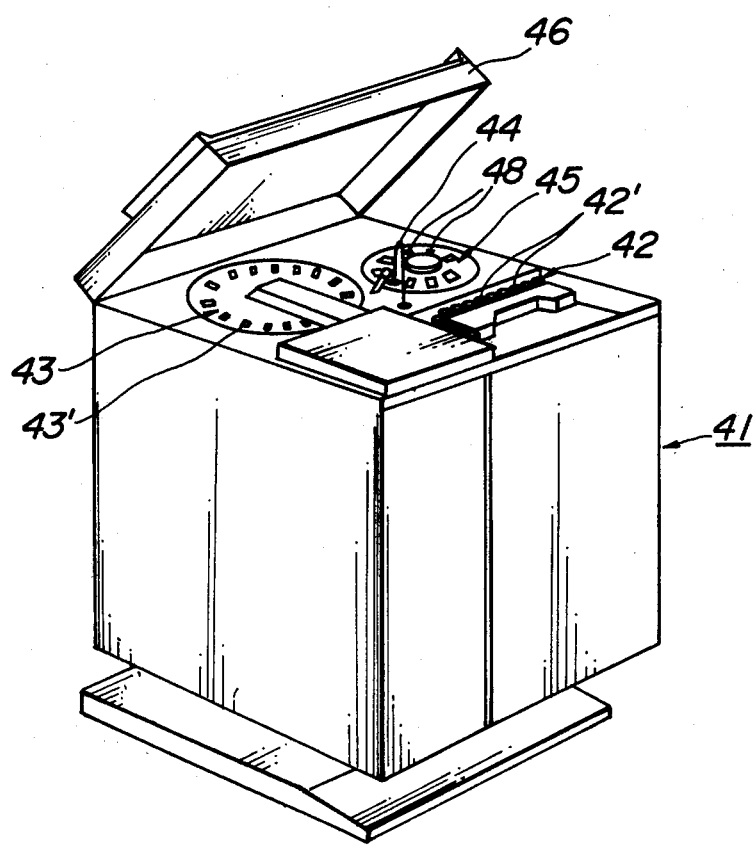
FIG. 4 is a perspective view of another embodiment of an automatic analyzing apparatus according to the invention.

FIG. 4 shows another embodiment of an automatic analyzing apparatus according to the invention. In the present embodiment, provision is made of a reagent vessel holder holding a plurality of reagent vessels therein. An apparatus main body 41 is provided at its upper surface with a sampler 42 operative to intermittently transfer along a given passage a plurality of sample cups 42' containing various kinds of collected samples. The samples to be transferred in succession by the sampler 42 are injected in succession to a plurality of reaction cuvettes 43' held by a reaction disc 43 by a given amount by means of a sample syringe (not shown). The reaction cuvettes 43' are arranged along the same circle having a center at the rotary axis of the reaction disc 43 operative to be intermittently rotated with a constant period by means of a pulse motor (not shown). To each reaction cuvette 43' arranged on the reaction disc 43 and received the sample is injected a given amount of reagent in response to the analysis item by means of a probe 44 which constitutes a reagent syringe at a given position. As a result, a test liquid is formed in each cuvette 43'.

In the present invention, analysis on a plurality of given items is effected at one time by means of one analyzing operation. For this purpose, a plurality of reagent vessel 48 for containing reagents necessary for the analysis on the plurality of given items are held by a reagent vessel holder 45. The reagent vessel holder 45 is detachably mounted on a guide plate 57 secured to a base plate 54.

The test liquid prepared from the sample and reagent and contained in the reaction cuvette 43′ is transferred to a given photometric position where the light which has passed through the filter for transmitting the light having a given wave length in response to the analysis item passes through the test liquid to effect the colorimetric measurement. Alternatively, the test liquid in the reaction cuvette 43′ is sucked into a flow cell (not shown) on which is incident the light which has passed through the above mentioned filter to effect the colorimetric measurement. The quantitative analysis is effected by the value thus measured and the concentration conversion factor in response to the analysis item. The apparatus main body 41 is provided at its upper surface with a cover 46 operative to be opened and closed for the purpose of maintaining the reaction temperature of the test liquid substantially constant.

Figure 5:
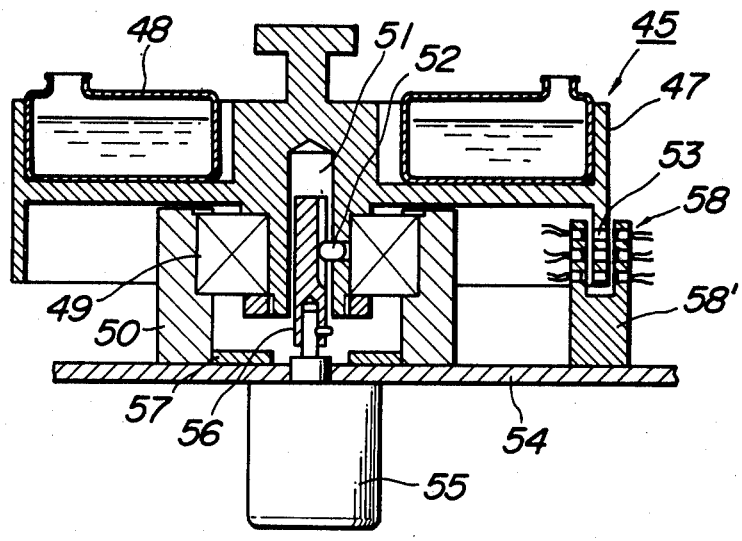
FIG. 5 is a cross-sectional view of a reagent vessel holder set on a mounting member of the automatic analyzing apparatus shown in FIG. 4.
Figure 6:
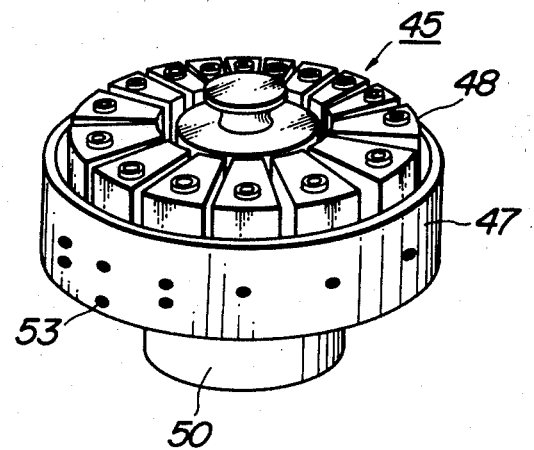
FIG. 6 is a perspective view of the reagent vessel holder shown in FIG. 5.

FIG. 5 shows in section the base plate 54 and reagent vessel holder 45 set thereon of the automatic analyzing apparatus shown in FIG. 4. FIG. 6 shows the reagent vessel holder 45 in itself. The reagent vessel holder 45 is composed of a turntable 47 which encloses therein a plurality of reagent vessels 48 arranged along the same circle having a center at the rotary axis of the reagent vessel holder 45 in a given order. The reagent vessels 48 contain reagents necessary for analysis on a plurality of given items. The turntable 47 is rotatably journalled through a bearing 49 by a holding member 50. The turntable 47 is provided at its center portion with a bore 51 adapted to insert therein a driving shaft 56 connected to the output shaft of a motor 55. Into a portion of the bore 51 is projected a pin 52. The turntable 47 is provided at its side wall with discrimination holes 53 for discriminating the analysis items which can be analyzed by the reagents in the reagent vessel 48 held by the turntable 47.

The reagent vessel holder 45 is mounted on the base plate 54 to which is secured the motor 55 and guide plate 57. To the output shaft of the motor 55 is secured the driving shaft 56 inserted into the bore 51 provided in the reagent vessel holder 45 and provided along its lengthwise direction with a slit slidably engageable with the pin 52. The guide plate 57 is secured to the upper surface of the base plate 54 and adapted to be engaged with the inner surface of the holding member 50 of the reagent vessel holder 45. A detector 58 is composed of photocouplers mounted on a supporting member 58′ secured to the base plate 54 and cooperative with the discrimination holes 53 provided in the reagent vessel holder 45.

In the case of setting the reagent vessel holder 45 on the base plate 54, the holding member 50 is brought into engagement with the guide member 57 secured to the base plate 54 and the pin 52 projected into the bore 51 engages with the slit provided in the driving shaft 56. If the motor 55 is energized to rotate the turntable 47 by a given distance, it is possible to move the reagent vessel 48 containing the desired reagent to a given injection position of the probe 44 for constituting the reagent syringe as shown in FIG. 4.

In the present embodiment, the detector 58 is composed of three photocouplers. The lowest photocoupler is used to deliver an original point signal for indexing the reagent vessel holder 47 corresponding to organic ability to be examined. The original point signal thus delivered from the lowest photocoupler causes to move the desired reagent vessel 48 arranged in the given order to a given injection position. The other two photocouplers function to discriminate the reagent vessels 48 one from the other.

As shown in FIGS. 7A, 7B and 7C, the three discrimination holes 53 provided in the reagent vessel holder 45 are used such that the lowest hole shown by a full line in FIG. 7A can deliver the original point signal and that a combination of the other two upper holes can discriminate three kinds of reagent vessels 48 one from the other as shown by full line and dotted lines holes in FIGS. 7A, 7B and 7C.

FIG. 8 shows a control circuit for the automatic analyzing apparatus shown in FIG. 4. As described above, the detector 58 functions to discriminate the reagent vessel holder 45 set on the base plate 54 and deliver the discrimination signal. The discrimination signal is supplied through an interface 59 to a control device 60. In a memory 61 have beforehand been stored the analysis condition such as the amount of sample to be injected, amount of reagent to be injected, photometric wave length, concentration conversion factor or the like for each of all of the analysis items (in general more than 30 items) by means of a well known means. The control device 60 functions to read out from the memory 61 each analysis condition of the plurality of given analysis items (in general 6 to 12 items) which can be analyzed by the reagent vessel 48 set in the discriminated reagent vessel holder 45 on the basis of the discriminating signal from the detector 58. Based on the analysis condition read out from the memory 61, the operation of each member of the sample syringe, reagent syringe, rotation of the reagent vessel holder 45, selection of the optical filter or the like is controlled through the interface 62 and each driver 63 and a given concentration conversion factor is selected to deliver the desired analysis data as an output.

As stated hereinbefore, the automatic analyzing apparatus according to the invention is capable of precisely setting a plurality of desired analysis items by a simple operation of setting onto a mounting member a reagent vessel holder for holding a plurality of reagent vessels containing given reagents necessary for a plurality of desired analysis item. As a result, the invention can prepare a desired reagent vessel holder in response to a plurality of analysis items necessary for examining hepatic ability, kidney ability or the like.

What is claimed is:

1. An automatic analyzing apparatus comprising:
   means for containing a plurality of samples to be analyzed in a plurality of containers;
   means for delivering each of the samples into respective reaction vessels;
   a plurality of reagent vessels containing plural kinds of reagents for effecting a plurality of analysis items;
   a reagent vessel holder comprising a turntable for holding said plurality of reagent vessels along a circumference thereof;
   a delivery device for delivering into the reaction vessels a reagent contained in a reagent vessel which is indexed at a delivery position;
   means for rotating said reagent vessel holder in such a manner that the reagent vessels arranged in the reagent vessel holder are passed through said delivery position;

first indicia means provided in said reagent vessel holder for denoting an original point of the reagent vessel holder with respect to said delivery position;

second indicia means provided in said reagent vessel holder for discriminating the kind of the reagents;

means for detecting said first and second indicia means formed in said reagent vessel holder to generate an original point signal and a command signal for discriminating the kind of the reagent, respectively;

means for storing a plurality of analysis conditions for all analysis items to be effected by the apparatus, said analysis conditions including an amount of sample to be delivered into the reaction vessel, an amount of reagent to be delivered into the reaction vessel and photometric wavelength;

means for selecting in response to said command signal one of said plurality of the analysis conditions stored in said storing means, the selected analysis condition being related to an analysis item using the relevant reagent denoted by said command signal; and means for controlling said rotating means under the control of said original point signal and for controlling said delivering means in response to the analysis condition read out from said storing means.

2. The apparatus according to claim 1, wherein said reagent vessel holder is detachably engaged with the said rotating means.

3. The apparatus according to claim 2, wherein said rotating means comprises a base plate, a guide plate secured to upper surface of the base plate and a motor secured to a lower surface of the base plate, and said reagent vessel holder further comprises a holding member detachably engageable with said guide plate, a bearing arranged between the turntable and holding member and a post member provided in said turntable detachably coupled with said motor.

4. The apparatus according to claim 1, wherein said first and second indicia means are formed by indicia discrimination holes provided in the reagent vessel holder.

5. The apparatus according to claim 4, wherein: said detecting means comprises a detector composed of photocouplers mounted in a supporting member secured to an apparatus base plate and cooperative with said indicia discrimination holes provided in a reagent vessel holder so as to photoelectrically read out a reagent vessel corresponding to organic ability to be examined and also read out a plurality of reagent vessels held by a reagent vessel holder.

6. The apparatus according to claim 1, wherein: said controlling means is connected through an interface to said detecting means and through said storing means to an input keyboard, said controlling means being connected through drivers to pulse motors for driving a filter inserted into a photometric passage and for driving a syringe for delivering reagent and sample into a reaction cuvette.

7. An automatic analyzing apparatus comprising:

means for containing a plurality of samples to be analyzed in a plurality of containers;

means for delivering each of the samples into respective reaction vessels;

a plurality of reagent vessels containing plural kinds of reagents for effecting a plurality of analysis items;

reagent vessel holder means for holding said plurality of reagent vessels;

a delivery device for delivering into the reaction vessels a reagent contained in a reagent vessel which is indexed at a delivery position;

means for moving said reagent vessel holder means in such a manner that the reagent vessels arranged in the reagent vessel holder means are moved to said delivery position;

first indicia means associated with said reagent vessel holder means for denoting the indexing position of said reagent vessel holder means with respect to said delivery position;

second indicia means associated with said reagent vessel holder means for distinguishing as to the kind of the reagents;

means for detecting said first and second indicia means associated with said reagent vessel holder means to generate an indexing signal and a command signal for distinguishing the kind of the reagent;

means for storing a plurality of analysis conditions for all analysis items to be effected by the apparatus;

means for selecting in response to said command signal one of said plurality of the analysis conditions stored in said storing means, the selected analysis condition being related to an analysis item using the relevant reagent denoted by said command signal; and means for controlling said moving means under the control of said indexing signal and for controlling said delivering means and said delivery device in response to the analysis condition read out from said storing means;

whereby said detecting means operates to generate a command signal which is responded to by said selecting means which selects an analysis condition from said storing means such that an analysis is performed automatically.

8. The apparatus of claim 7 wherein said primary indicia means are utilized for determining the analysis items which can be analyzed by a reagent in said reagent vessel.

9. The apparatus of claim 7 wherein said analysis conditions include an amount of sample to be delivered into said reaction vessel and an amount of reagent to be delivered into said reaction vessel.

* * * * *